United States Patent [19]
Smetana

[11] 3,959,393
[45] May 25, 1976

[54] PREPARATION OF 1,2-DIHYDROXY COMPOUNDS

[75] Inventor: Richard D. Smetana, Beacon, N.Y.

[73] Assignee: Texaco Inc., New York, N.Y.

[22] Filed: Aug. 4, 1975

[21] Appl. No.: 601,777

Related U.S. Application Data

[63] Continuation of Ser. No. 818,779, April 23, 1969.

[52] U.S. Cl. .................. 260/621 G; 260/621 C; 260/625; 260/479 R
[51] Int. Cl.² ............... C07C 39/06; C07C 39/08
[58] Field of Search ............ 260/621 G, 621 R, 625, 260/621 C, 479 R

[56] References Cited
OTHER PUBLICATIONS
Bailey Chem. Revs. Vol. 58 "The Reactions of Ozone with Organic Compounds," pp. 932, 959, 960, 986, 992 and 993 (1958).
Hansen, Acta Chem. Scand. 17, pp. 1375–1379 1963.

Primary Examiner—James O. Thomas, Jr.
Assistant Examiner—W. B. Lone
Attorney, Agent, or Firm—T. H. Whaley; C. G. Ries; Robert A. Kulason

[57] ABSTRACT

Method of preparing a 1,2-dihydroxy compound of the formula:

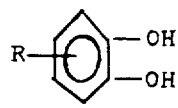

where R is hydrogen or alkyl comprising contacting a naphthalene compound of the formula:

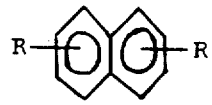

where R is as heretofore defined with ozone, alkanoic acid and a mineral acid and hydrolyzing the resultant intermediates to form said 1,2-dihydroxy compound.

3 Claims, No Drawings

PREPARATION OF 1,2-DIHYDROXY COMPOUNDS

This is a continuation of application Ser. No. 818,779, filed Apr. 23, 1969.

BACKGROUND OF INVENTION

The subject invention is in the field of art relating to the production of 1,2-dihydroxybenzene compounds.

In the past, these compounds were prepared by first catalytically chlorinating benzene or alkylbenzene to form chlorobenzene or its alkyl counterparts, heating the chlorobenzene compound with dilute sodium hydroxide under high pressure in a continuous tubular system of copper to form a chlorophenol, separating out the o-chlorophenol isomer, and hydrolyzing the o-chlorophenol in an aqueous solution of sodium and strontium hydroxides in the presence of copper to form the 1,2-dihydroxy compound. Although this method produced dihydroxybenzenes in satisfactory quantities, it was relatively complex requiring a number of chemical steps which undesirably increased the cost of the dihydroxy product. There was, therefore, a need for a simplified procedure of producing a dihydroxy compound from a basic hydrocarbon.

SUMMARY OF INVENTION

I have discovered, and this constitutes my invention, a method of producing dihydroxybenzene compounds from a basic hydrocarbon utilizing substantially fewer steps than required in many of the prior processes with the attendant result of a reduction in cost of manufacture. More specifically, my method comprises contacting a naphthalene compound of the general formula:

where R is hydrogen or alkyl of from 1 to 10 carbons with ozone in the presence of an alkanoic acid of from 2 to 10 carbons and a mineral acid and hydrolyzing the resultant product to form a 1,2-dihydroxy product of the formula:

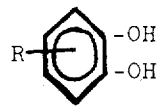

where R is as heretofore defined.

DETAILED DESCRIPTION OF THE INVENTION

Specifically, the method of the invention comprises first reacting under substantially anhydrous conditions a mixture of naphthalene compound, ozone, alkanoic and mineral acid, all as heretofore defined, at a temperature between about −100° and 150°C. utilizing a mole ratio of naphthalene compound to ozone of between about 1:1 and 1:3, naphthalene compound to alkanoic acid of between about 1:1 and 1:100, and naphthalene compound to mineral acid between about 100:1 and 1:1. The reaction period in this first step is normally between about 1 and 3 hours although longer and shorter periods may be employed, the exact time period is dependent upon the yield desired under the conditions utilized. Hereinbefore and hereinafter by the term "substantially anhydrous" a water content of less than 1 wt. % based on the reaction mixture is intended.

The formed intermediates resulting from the ozone-acid step are then subjected to hydrolysis. Hydrolysis can be accomplished by contacting the products with between about 50 and 95 wt. % (based on said products) of a hydrolyzing medium comprising an aqueous solution containing between about 0.01 and 10 wt. % of a mineral acid or inorganic base. The hydrolysis is advantageously conducted at a temperature between about 0 and 200°C.

The resultant dihydroxybenzene products are recovered from the hydrolysis mixture in a purified state by standard means such as fractional distillation, filtration, recrystallization, washing, complexing and combinations thereof.

In a non-preferred embodiment of the invention, the naphthalene reactant may be sequentially contacted with ozone to form an ozonide intermediate, followed by contacting the formed ozonide with the mineral acid-alkanoic acid combination as heretofore defined to form an acyloxybenzene and then hydrolyzing the resultant reaction mixture as heretofore described to form the desired dihydroxybenzene products.

Under preferred conditions, the ozonation reaction is conducted in the presence of solvent desirably constituting between about 50 and 95 wt. % of the reaction mixture. Suitable solvents are chloroform, carbon tetrachloride, but most preferably alkanoic acid anhydride of from 4 to 20 carbons such as acetic anhydride, propanoic anhydride, or hexanoic anhydride. Acetic anhydride is most preferred. When anhydride is employed it functions not only as solvent but aids in the maintenance of the anhydrous nature of the reaction as well as aiding in maintaining the acidity of the reaction during ozonation thereby preventing unnecessary consumption of the mineral acid.

During ozonation and hydrolysis the reaction mixture is preferably stirred in order to facilitate contact of the individual ingredients therein.

The following equations further illustrate the method of the invention utilizing naphthalene, acetic acid, sulfuric acid, ozone and sodium hydroxide as reaction ingredients:

1) 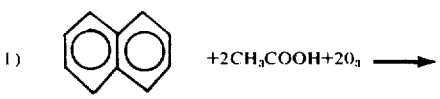

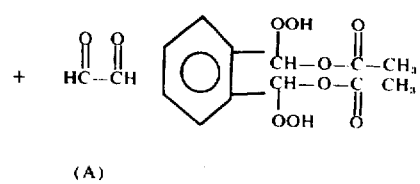

(A)

2)

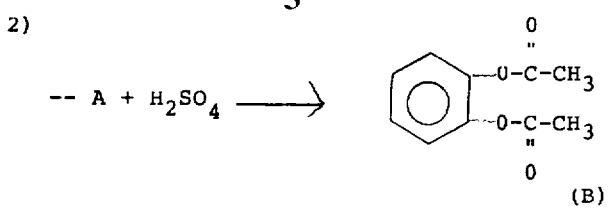

3)

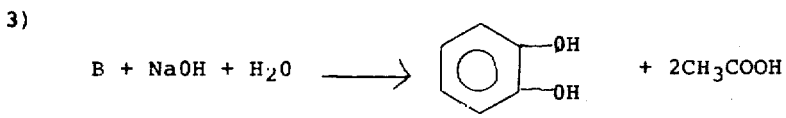

In the reaction specific examples of the naphthalene reactants contemplated herein are naphthalene; 1,5-dimethyl naphthalene; 1,5-diisoamylnaphthalene; and 2,6-didecylnaphthalene.

Specific examples of the dihydroxy products respectively resulting therefrom are catechol, 1,2-dihydroxy-3-methylbenzene; 1,2-dihydroxy-3-isoamylbenzene and 1,2-dihydroxy-4-decylbenzene.

The ozone employed is usually in admixture with air oxygen or inert gas such as nitrogen in a quantity of between about 0.1 and 15 mole %.

In regard to the mineral acid reactants in the first step reaction, suitable examples are concentrated sulfuric acid, perchloric acid and hydrochloric acid.

Examples of the alkanoic acid reactants contemplated herein are acetic, propanoic, butanoic and hexanoic acid with acetic acid being preferred.

In the hydrolysis step examples of the strong water soluble bases and acids contemplated herein are sodium hydroxide, potassium hydroxide, sulfuric acid, hydrochloric acid and perchloric acid.

The following example further illustrates the method of the invention but is not to be construed as a limitation thereof.

EXAMPLE 1

To a 3-neck, 500 ml. round-bottomed flask there is fitted a thermometer, dry ice condenser and gas sparger. In the flask there is placed a magnetic stirring bar, 100 grams of chloroform, 100 grams of acetic anhydride, 50 grams of acetic acid, 25.6 grams of (0.2 mole) naphthalene and 3 mls. of concentrated sulfuric acid. The resultant solution is lowered to 10°C. and a stream of 3.0 mole % ozone in oxygen is passed through the solution for 3.7 hours at a rate of 600 mls./minute. The resultant acidic organic solution is twice washed with 300 mls. of ice water then 500 mls. of dilute aqueous (5 wt. %) sodium bicarbonate and 500 mls. of water again and the aqueous washings are set aside. The chloroform layer is dried over magnesium sulfate overnight, and the solvent is removed at reduced pressure and rotary evaporator. The solutions are then fractionally distilled and the fractions are submitted to both infrared and gas chromatographic analysis. They are found to show the presence of catechol diacetate.

The set aside aqueous layers are made just alkaline with 10 wt. % aqueous sodium hydroxide (dark color forms) and a saturated aqueous solution of lead acetate is added until no further precipitate forms. The solids are filtered and dried in an oven at 100°C. at reduced pressure (300 mm Hg.) for three days. The total weight of the precipitate is 56.8 grams. Four solids respectively are weighed and are each mixed with an equal weight of acetic anhydride, 3 drops of sulfuric acid and heated to reflux for 2 hours. Chromatographic analysis shows the presence of catechol diacetate. All recovered catechol diacetate fractions are then combined totaling an amount of 7.0 grams and are stirred with about 0.1 wt. % concentrated sulfuric acid in 100 grams of water at 25°C. and 5.0 grams of 1,2-dihydroxybenzene are recovered from the resultant mixture by extraction with four 25 ml. portions of diethylether, the ether extracts being combined and the ether removed via distillation leaving the catechol as residue.

I claim:

1. A method of preparing a dihydroxybenzene compound of the formula:

where R is hydrogen or primary alkyl of from 1 to 10 carbons comprising first contacting under substantially anhydrous conditions a naphthalene compound of the formula:

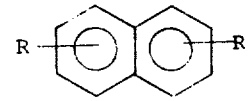

where R is as heretofore defined with ozone and a mixture of first mineral acid and alkanoic acid of from 2 to 10 carbons at a temperature of about 10°C. utilizing a mole ratio of said naphthalene compound to ozone of between about 1:1 and 1:3, said naphthalene compound to alkanoic acid of between about 1:1 and 1:100 and said naphthalene compound to said mineral acid of between about 100:1 and 1:1 to form an acyloxybenzene intermediate and hydrolyzing said intermediate with an aqueous solution of an agent selected from the group consisting of a second mineral acid and inorganic base to form said dihydroxybenzene.

2. A method in accordance with claim 1 wherein said dihydroxybenzene is catechol, said naphthalene compound is naphthalene, said first and second mineral acid and said agent are sulfuric acid, said alkanoic acid is acetic acid and wherein said first contacting additionally takes place in the presence of between about 50 and 95 wt. % of acetic anhydride based on the reaction mixture in said first contacting.

3. A method according to claim 1 wherein said hydrolyzing said aqueous solution contains between about 0.01 and 10 wt. % of said agent and said aqueous solution comprises between about 50 and 95 wt. % of the hydrolysis mixture.

* * * * *